US00PP30377P2

(12) United States Plant Patent
Koot

(10) Patent No.: US PP30,377 P2
(45) Date of Patent: Apr. 9, 2019

(54) ***CALIBRACHOA* PLANT NAMED 'DOCABLAQ'**

(50) Latin Name: *Calibrachoa X hybrida*
Varietal Denomination: Docablaq

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,840

(22) Filed: Jan. 3, 2018

(51) Int. Cl.
*A01H 5/02* (2018.01)

(52) U.S. Cl.
USPC ..... Plt./413

(58) Field of Classification Search
USPC ..... Plt./413
See application file for complete search history.

*Primary Examiner* — Annette H Para
(74) *Attorney, Agent, or Firm* — C. A. Whealy

(57) ABSTRACT

A new and distinct cultivar of *Calibrachoa* plant named 'Docablaq', characterized by its semi-upright to outwardly spreading, trailing and decumbent plant habit; vigorous growth habit; freely branching habit; early and freely flowering habit; large flowers with light violet and dark purple bi-colored petals; and good garden performance.

1 Drawing Sheet

Botanical designation: *Calibrachoa* X *hybrida.*
Cultivar denomination: 'DOCABLAQ'.

BACKGROUND OF THE INVENTION

The present invention relates to a new and distinct cultivar of *Calibrachoa* plant, botanically known as *Calibrachoa* X *hybrida* and hereinafter referred to by the name 'Docablaq'.

The new *Calibrachoa* plant is a product of a planned breeding program conducted by the Inventor in Rheinberg, Germany. The objective of the breeding program is to create new early-flowering and vigorous *Calibrachoa* plants with large attractive flowers, The new *Calibrachoa* plant originated from a cross-pollination made by the Inventor in July, 2014 in Rheinberg, Germany of a proprietary selection of *Calibrachoa* X *hybrida* identified as code number AA13-000848-002, not patented, as the female, or seed, parent with a proprietary selection of *Calibrachoa* X *hybrida* identified as code number AA13-005114-008, not patented, as the male, or pollen, parent. The new *Calibrachoa* plant was discovered and selected by the Inventor as a single flowering plant from within the progeny of the stated cross-pollination in a controlled greenhouse environment in Rheinberg, Germany in May, 2017.

Asexual reproduction of the new *Calibrachoa* plant by vegetative terminal cuttings in a controlled greenhouse environment in Rheinberg, Germany since June, 2017 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Docablaq'. These characteristics in combination distinguish 'Docablaq' as a new and distinct *Calibrachoa* plant:

1. Semi-upright to outwardly spreading, trailing and decumbent plant habit.
2. Vigorous growth habit.
3. Freely branching habit.
4. Early and freely flowering habit.
5. Large flowers with light violet and dark purple bi-colored petals.
6. Good garden performance.

The new *Calibrachoa* can be compared to plants of the female parent selection. Plants of the new *Calibrachoa* differ primarily from plants of the female parent selection in the following characteristics:

1. Plants of the new *Calibrachoa* are more vigorous than plants of the female parent selection.
2. Plants of the new *Calibrachoa* flower earlier than plants of the female parent selection.
3. Plants of the new *Calibrachoa* and the female parent selection differ in flower color as plants of the female parent selection have pink and light purple bi-colored flowers.

The new *Calibrachoa* can be compared to plants of the male parent selection. Plants of the new *Calibrachoa* differ primarily from plants of the male parent selection in the following characteristics:

1. Plants of the new *Calibrachoa* flower earlier than plants of the male parent selection.
2. Plants of the new *Calibrachoa* have larger flowers than plants of the male parent selection.
3. Plants of the new *Calibrachoa* and the male parent selection differ in flower color as plants of the male parent selection have pink-colored flowers.

Plants of the new *Calibrachoa* can be compared to plants of *Calibrachoa* sp. 'MiniFamous Neo Pink with Red Eye', not patented. In side-by-side comparisons, plants of the new *Calibrachoa* differ primarily from plants of 'MiniFamous Neo Pink with Red Eye' in the following characteristics:

1. Plants of the new *Calibrachoa* are larger and more vigorous than plants of 'MiniFamous Neo Pink with Red Eye'.
2. Plants of the new *Calibrachoa* have larger leaves than plants of 'MiniFamous Neo Pink with Red Eye'.
3. Plants of the new *Calibrachoa* have larger flowers than plants of 'MiniFamous Neo Pink with Red Eye'.
4. Plants of the new *Calibrachoa* and 'MiniFamous Neo Pink with Red Eye' differ in flower color as plants of 'MiniFamous Neo Pink with Red Eye' have light purple-colored flowers.

BRIEF DESCRIPTION OF THE PHOTOGRAPH

The accompanying colored photograph illustrates the overall appearance of the new *Calibrachoa* plant showing the colors as true as it is reasonably possible to obtain in colored reproductions of this type. Colors in the photograph may differ slightly from the color values cited in the detailed botanical description which accurately describe the colors of the new *Calibrachoa* plant. The photograph is a side perspective view of a typical flowering plant of 'Docablaq' grown in a container.

DETAILED BOTANICAL DESCRIPTION

The aforementioned photograph and following observations, measurements and values describe plants grown during the spring and summer in 22-cm containers in a glass-covered greenhouse in Rheinberg, Germany and under cultural practices typical of commercial *Calibrachoa* production. During the production of the plants, day and night temperatures averaged 18° C. and light levels averaged 4,500 lux. Rooted young plants were pinched one time three weeks after planting and were 16 weeks old when the photograph and description were taken. In the following description, color references are made to The Royal Horticultural Society Colour Chart, 2007 Edition, except where general terms of ordinary dictionary significance are used.

Botanical classification: *Calibrachoa* X *hybrida* 'Docablaq'.

Parentage:

*Female, or seed, parent*.—Proprietary selection of *Calibrachoa* X *hybrida* identified as code number AA13-000848-002, not patented.

*Male, or pollen, parent*.—Proprietary selection of *Calibrachoa* X *hybrida* identified as code number AA13-005114-008, not patented.

Propagation:

*Type*.—By vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 158A in color, actual color of the roots is dependent on substrate composition, water quality, fertilizers, substrate temperature and age of roots.

*Rooting habit*.—Freely branching; dense.

Plant description:

*Plant and growth habit*.—Semi-upright to outwardly spreading to trailing and decumbent plant habit; freely branching habit with about 10 to 15 primary lateral branches each with about eight to ten secondary lateral branches developing per plant; pinching enhances branching; dense and full appearance; vigorous growth habit; moderate growth rate.

*Plant height, soil level to top of foliar plane*.—About 24 cm.

*Plant height, soil level to top of floral plane*.—About 26 cm.

*Plant diameter* (*spread of plant*).—About 90 cm.

Lateral branch description:

*Length*.—About 15 cm.

*Diameter*.—About 3 mm.

*Internode length*.—About 1.4 cm.

*Strength*.—Strong.

*Aspect*.—Initially upright to outwardly spreading to trailing and decumbent.

*Texture and luster*.—Pubescent; semi-glossy.

*Color, developing*.—Close to 144B; at the internodes, close to 144A.

*Color, developed*.—Close to 144A.

Leaf description:

*Arrangement*.—Before flowering, alternate, and after flowering, opposite; simple.

*Length*.—About 3 cm.

*Width*.—About 7.5 mm.

*Shape*.—Oblanceolate.

*Apex*.—Rounded.

*Base*.—Cuneate.

*Margin*.—Entire.

*Texture and luster, upper and lower surfaces*.—Pubescent; matte.

*Venation pattern*.—Pinnate; arcuate.

*Color*.—Developing leaves, upper surface: Close to 138A. Developing leaves, lower surface: Close to 137C. Fully expanded leaves, upper surface: Close to 137B; venation, close to 144B. Fully expanded leaves, lower surface: Close to 147B; venation, close to 144B.

*Petioles*.—Length: About 2 mm. Diameter: About 1.2 mm. Strength: Moderately strong. Texture and luster, upper and lower surfaces: Pubescent; matte. Color, upper and lower surfaces: Close to 144B.

Flower description:

*Flower arrangement and habit*.—Single salverform flowers arising from leaf axils; freely flowering habit with usually about 400 to 500 flowers developing per plant during the flowering season; flowers face upright to outwardly.

*Fragrance*.—None detected.

*Natural flowering season*.—Early flowering habit, plants of the new *Calibrachoa* initiate and develop flowers about six weeks after planting; plants flower continuously from the spring throughout the summer in Germany.

*Flower longevity*.—Individual flowers last about seven to ten days on the plant; flowers not persistent.

*Flower diameter*.—About 4.2 cm.

*Flower depth* (*height*).—About 3.4 cm.

*Flower throat diameter*.—About 1.1 cm.

*Flower tube length*.—About 2.2 cm.

*Flower tube diameter*.—About 4 mm.

*Flower buds*.—Length: About 2.4 cm. Diameter: About 4.5 mm. Shape: Elongated oblong. Texture and luster: Rippled, pubescent; matte. Color: Close to 145C and 155A.

*Corolla*.—Arrangement: Five petals fused at the base and opening into a flared trumpet. Petal length from throat: About 1.6 cm. Petal lobe width: About 2 cm. Petal shape: Roughly spatulate. Petal apex: Rounded. Petal margin: Entire; slightly undulate. Petal texture and luster, upper and lower surfaces: Smooth, glabrous; matte. Throat texture: Smooth, glabrous. Tube texture: Smooth, glabrous. Color: Petal, when opening, upper surface: Close to 76A; towards the throat, close to 79A. Petal, when opening, lower surface: Close to 76C. Petal, fully opened, upper surface: Distally, close to 84D; towards the throat, close to 79A; venation, close to 79A; color becoming closer to N81A with development. Petal, fully opened, lower surface: Close to 69D; venation, close to 200A; color does not change with development. Throat: Close to 7A; venation, close to 200C. Tube: Close to 145C; venation, close to 200A.

*Calyx*.—Arrangement: Star-shaped calyx with five sepals; sepals fused at the base. Sepal length: About 1.8 cm. Sepal width: About 5 mm. Sepal shape: Lanceolate. Sepal apex: Acute. Sepal margin: Entire. Sepal texture and luster, upper and lower surfaces: Pubescent; matte. Color: When developing and fully developed, upper surface: Close to 146A. When developing and fully developed, lower surface: Close to 146B.

*Peduncles*.—Length: About 1.6 cm. Diameter: About 2 mm. Angle: About 45° from stem axis. Strength: Moderately strong. Texture and luster: Pubescent; matte. Color: Close to 143C.

*Reproductive organs*.—Stamens: Quantity: Five per flower. Filament length: About 8 mm. Filament color: Close to 145C. Anther length: About 1 mm. Anther shape: Ellipsoidal. Anther color: Close to 9A. Pollen amount: Scarce. Pollen color: Close to 9A. Pistils: Quantity: One per flower. Pistil length: About 1 cm. Style length: About 9 mm. Style color: Close to 144D. Stigma diameter: About 0.3 mm. Stigma shape: Ellipsoidal. Stigma color: Close to 143C. Ovary color: Close to 146C. Fruits: Quantity produced per plant: About 350 during the flowering season. Length: About 6 mm. Diameter: About 4 mm. Texture: Smooth, glabrous. Color: Close to N199C. Seeds: Quantity per flower: About 20. Length: About 0.8 mm. Diameter: About 0.8 mm. Texture: Smooth, glabrous. Color: Close to 200A.

Garden performance: Plants of the new *Calibrachoa* have been observed to have good garden performance and to tolerate wind, rain, temperatures ranging from about 3° C. to about 28° C. and to be suitable for USDA Hardiness Zone 11.

Pathogen & pest resistance: Plants of the new *Calibrachoa* have not been observed to be resistant to pathogens and pests common to *Calibrachoa* plants to date.

It is claimed:

1. A new and distinct *Calibrachoa* plant named 'Docablaq' as illustrated and described.

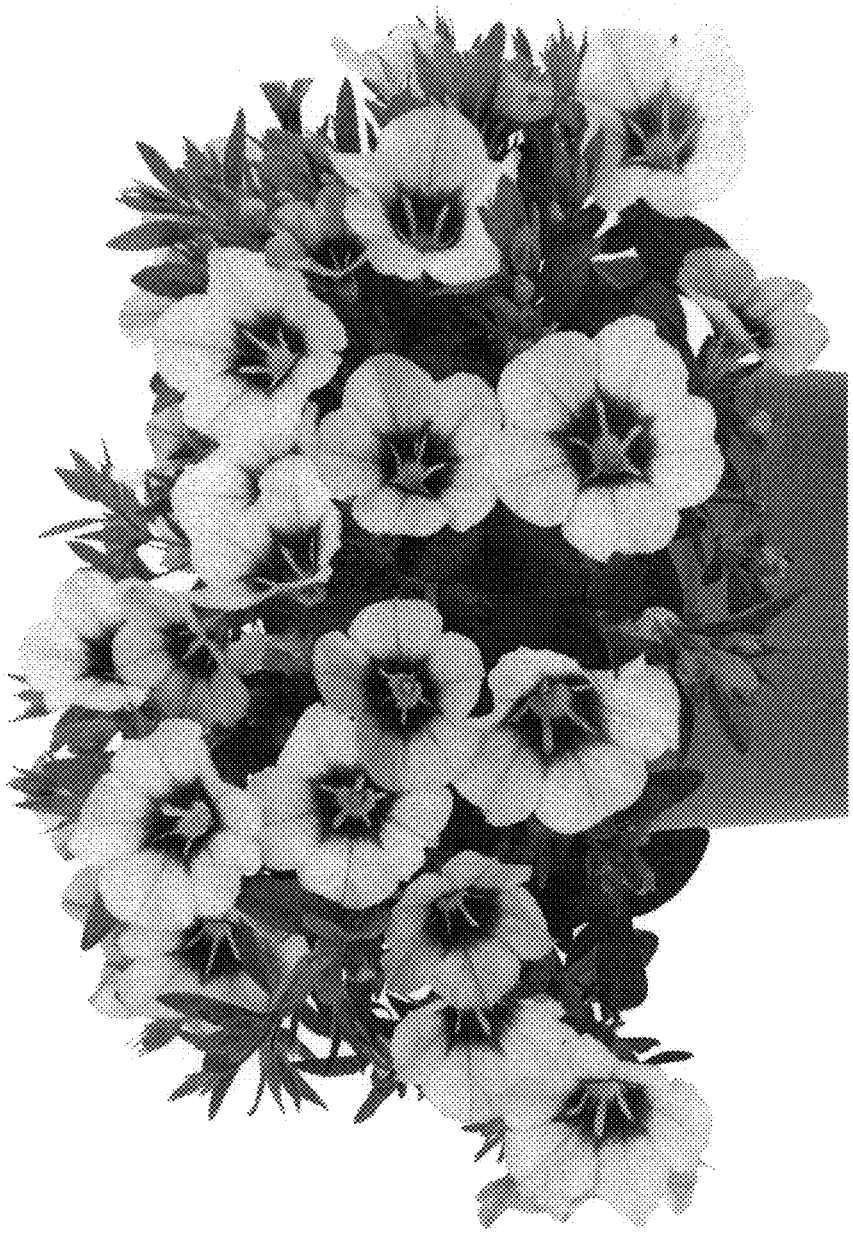

* * * * *